United States Patent [19]
Ohnishi et al.
[11] Patent Number: 4,534,966
[45] Date of Patent: Aug. 13, 1985

[54] COMPOSITION FOR TREATING INFECTIOUS DISEASES, GOUT OR ARTERIOSCLEROSIS CONTAINING HUMAN PEPSIN AND/OR HUMAN LEUKOCYTE PEPSIN-LIKE ENZYME AND METHOD FOR USING SAME

[75] Inventors: Haruo Ohnishi, Funabashi; Hiroshi Kosuzume, Yokohama; Yasuo Suzuki, Kawaguchi; Ei Mochida, Tokyo, all of Japan

[73] Assignee: Mochida Pharmaceutical Co., Ltd., Tokyo, Japan

[21] Appl. No.: 552,613

[22] Filed: Nov. 17, 1983

[30] Foreign Application Priority Data

Nov. 20, 1982 [JP] Japan ................................ 57-203990

[51] Int. Cl.[3] ................................ A61K 37/54
[52] U.S. Cl. ................................ 424/94
[58] Field of Search ................................ 424/94

[56] References Cited

U.S. PATENT DOCUMENTS

| | | | |
|---|---|---|---|
| 2,930,736 | 3/1960 | Sullivan et al. | 424/94 |
| 4,272,522 | 6/1981 | Balazs | 424/94 |

OTHER PUBLICATIONS

Inoue et al., Chem. Abst., vol. 92 (1980), p. 174,585j.
Nothdurft, Chem. Abst., vol. 77 (1972), p. 147520t.

*Primary Examiner*—Sam Rosen
*Attorney, Agent, or Firm*—Parkhurst & Oliff

[57] ABSTRACT

There are provided a pharmaceutical composition having an effect to control phagocytic function, which comprises a pharmaceutically effective amount of human pepsin and/or a human leukocyte pepsin-like enzyme and a pharmaceutically acceptable carrier, and a therapeutic method using said composition. The pharmaceutical composition is useful for treatment of infectious diseases, gout and arteriosclerosis.

15 Claims, No Drawings

COMPOSITION FOR TREATING INFECTIOUS DISEASES, GOUT OR ARTERIOSCLEROSIS CONTAINING HUMAN PEPSIN AND/OR HUMAN LEUKOCYTE PEPSIN-LIKE ENZYME AND METHOD FOR USING SAME

BACKGROUND OF THE INVENTION

1. Field of the Invention

This invention relates to pharmaceutical compositions having an effect to control phagocytic function, which comprise human pepsin and/or a human leukocyte pepsin-like enzyme as an active ingredient.

2. Description of the Prior Art

One of the functions which the living body performs for maintaining homeostasis is the immune mechanism. It is known that foreign matter which has invaded from the outside or a substance which has become foreign matter in vivo can sometimes adversely affect the living body, and that the immune mechanism exerts an effect upon the attack and development of such diseases as infectious diseases, tumors, autoimmune diseases, etc. For that reason, there have lately been made attempts to treat these diseases by controlling the immune mechanism, and immunomodulators have been employed for treatment of tumors. However, the conventional immunomodulatory agents are drugs which mainly control the functions of lymphocytes which act as effectors for humoral immunity and cellular immunity, and there has been little research done on drugs which directly control phagocytic functions.

Phagocytes not only engulf and digest foreign matter which has invaded the living body, e.g. microorganisms such as virus, bacteria, eumycetes, etc., and foreign matter which has been generated in the body, e.g. tumors, etc., but also play an important role in controlling immune response by transferring information on said foreign matter to lymphocytes. Further, it is believed that gout and arteriosclerosis are brought about by uric acid or cholesterol deposits generated in the body, and it is presumed that phagocytes also participate in disposal of these deposits. Therefore, drugs having an effect to control phagocytic functions are expected to be effective as drugs for treating not only such diseases to which lymphocytic function-controlling agents have been conventionally applied but also such diseases as infectious diseases, tumors, arteriosclerosis, etc.

Since a drug having an effect to control phagocytic functions would be expected to be effective as a drug for treating such diseases as infectious diseases caused by virus, bacteria, eumycetes, etc., and gout, arteriosclerosis, etc., the present inventors have intensively studied in order to develop such a drug and have found that human pepsin and/or a human leukocyte pepsin-like enzyme exhibit an effect to control phagocyte-mediated immunity and improve infectious diseases, gout and arteriosclerosis, thereby having accomplished this invention.

SUMMARY OF THE INVENTION

Accordingly, an object of this invention is to provide a pharmaceutical composition which controls phagocytic function, comprising human pepsin and/or a human leukocyte pepsin-like enzyme together with a pharmaceutically acceptable carrier.

Another object of this invention is to provide a therapeutic agent for treating infectious diseases, gout and arteriosclerosis which comprises human pepsin and/or a human leukocyte pepsin-like enzyme together with a pharmaceutically acceptable carrier.

A further object of this invention is to provide a method for treating infectious diseases, gout or arteriosclerosis, which comprises administering a therapeutically effective amount of human pepsin and/or a human leukocyte pepsin-like enzyme to a patient suffering from infectious diseases, gout or arteriosclerosis.

The human pepsin and the human leukocyte pepsin-like enzyme which are active ingredients of the therapeutic agents of this invention have an effect to potentiate phagocytosis of phagocytes, an effect to potentiate phagocytes to transfer immune information to lymphocytes, an effect to promote phagocytosis of heterocytes by macrophages, an effect to potentiate bactericidal activity by neutrophiles, an effect to inhibit deposition of cholesterol onto artery walls and an effect to inhibit experimental disturbance in gait resulting from injection of a urate into the joint cavity.

DETAILED DESCRIPTION OF THE PREFERRED EMBODIMENTS

Human pepsin which is one of the active ingredients of this invention is a known enzyme (Etherington et al., Biochim. et Biophi, Acta, 236, 92 (1971)) and may be obtained from human gastric cells, human gastric juices, human urine, etc. by appropriately combining general methods commonly employed for purifying proteins, for example, salting out, adsorption chromatography using inorganic adsorbents, ion exchange chromatography using ion exchange resins, gel chromatography with a molecular sieve effect, etc. Further, it may be mass-produced by cultivation of cells obtained by fusion of pepsin-producing cells such as human gastric cells with cancer cells, or by genetic engineering procedures, for example, by preparing complementary DNA by employing messenger RNA of human pepsin as a mold and using a reverse transcriptase and then incorporating this DNA into Escherichia Coli, etc.

For example, the human pepsin used in this invention may be obtained according to a method of Seijffers et al., Amer. J. Physiol., 206, 1106 (1964) by passing human urine through a DEAE-cellulose column equilibrated with 0.1M acetate buffer (pH 5.3) to adsorb the human pepsin thereon, eluting it with the same buffer except that it further contains 0.3M sodium chloride, then concentrating the eluate and finally further purifying the concentrate by gel chromatography using Sephadex G-100 (trademark) swollen with 0.9% physiological saline. This human pepsin was found to have a molecular weight of 32,000–38,000 according to the analysis by gel chromatography using Sephadex G-100 (trademark), an isoelectric point of 1–3 as measured by amphorein isoelectric electrophoresis and a maximum absorption of 274 nm, gives a positive ninhydrin reaction and is readily soluble in water and insoluble in ether and chloroform.

On the other hand, the human leukocyte pepsin-like enzyme is an enzyme found by the present inventors (Patent Application: PCT JP82-00213) and may be obtained from human leukocytes or actinomycin D treated promyelocytic leukemia cells HL-60 strains, etc. by appropriately combining general methods commonly employed for purifying proteins, for example, salting out, adsorption chromatography using inorganic adsorbents, ion exchange chromatography using ion exchange resins, gel chromatography with a molecular sieve effect, etc. Further, it may be mass-produced by cultivation of cells obtained by fusion of pepsin-like enzyme producing cells such as human leukocytes with cancer cells, or by genetic engineering procedures, for example, by preparing complementary DNA by employing messenger RNA of the human leukocyte pepsin-like enzyme as a mold and using a reverse transcriptase and then incorporating this DNA into Escherichia Coli, etc.

For example, the human leukocyte pepsin-like enzyme may be obtained by homogenizing the aforesaid cultured cells to obtain a supernatant, passing the supernatant through a DEAE-cellulose column equilibrated with 0.1M acetate buffer (pH 5.3) to adsorb the human leukocyte pepsin-like enzyme, then eluting it with the same buffer except that it further contains 0.5M sodium chloride, concentrating the eluate, and finally further purifying the concentrate by gel chromatography using Sephadex G-100 swollen with 0.9% physiological saline. This human leukocyte pepsin-like enzyme was found to have a molecular weight of 35,000–41,000 by analysis by gel chromatography with Sephadex G-100 (trademark), an isoelectric point of 2.5–3.5 as measured by amphorein isoelectric electrophoresis and a maximum absorption of 278 nm, gives a positive ninhydrin reaction and is readily soluble in water and insoluble in ether and chloroform. Further, the human leukocyte pepsin-like enzyme exhibits high hydrolytic activity against hemoglobin in an acidic region of pH 7.0 or lower and its optimum pH is 2.0–3.5.

The effectiveness, toxicity, use method and dosage of each of the human pepsin and the human leukocyte pepsin-like enzyme are explained below.

EXPERIMENTAL EXAMPLE 1

Influence on Phagocytosis of Human Monocytes

Human peripheral monocytes ($10^6$ cells) attached on a culture surface were prepared from a suspension of peripheral leukocytes in Eagle minimum essential medium by culturing the cells in a plastic dish at 37° C. for 1 hour.

5 ml of Eagle minimum essential medium (Eagle MEM) supplemented with 10 v/v% fetal bovine serum and containing human pepsin or a human leukocyte pepsin-like enzyme was added to $10^6$ cells of human peripheral monocytes, and they were cultured at 37° C. After 20 hours, the medium was changed to Eagle MEM supplemented with 10% fetal bovine serum and containing human pepsin or a human leukocyte pepsin-like enzyme and $2\times10^6$ cells of heat-treated bread yeast, and culturing was effected for another 2 hours. After the culture, the rate of phagocytosis was calculated according to the following equation.

$$\text{Rate of Phagocytosis (\%)} = \frac{\text{Phagocytic Monocytes}}{\text{Total Monocytes}} \times 100$$

The results are set forth in Table 1.

TABLE 1

| Specimen | Concentration (μg/ml) | Rate of Phagocytosis (%) |
|---|---|---|
| Non (Eagle MEM only) | — | 37.3 ± 2.9 |
| Human Pepsin | 0.6 | 42.6 ± 2.8 |
| | 6 | 48.1 ± 2.3* |
| Human Leukocyte Pepsin-like Enzyme | 6 | 47.9 ± 2.5* |

*P <0.05 (Student's t-test)

The human pepsin and the human leukocyte pepsin-like enzyme promoted the phagocytosis of the yeast by human monocytes. From these results, it has been made clear that human pepsin and a human leukocyte pepsin-like enzyme potentiate phagocytosis of phagocytes.

EXPERIMENTAL EXAMPLE 2

Influence on Phagocytosis of Human Monocytes

Human peripheral monocytes ($10^6$ cells) attached on a culture surface were prepared from a suspension of peripheral leukocytes in Eagle MEM by culturing the cells in a plastic dish at 37° C. for 1 hour. 5 ml of Eagle MEM supplemented with 10 V/V% fetal bovine serum and containing a given amount of human pepsin or human leukocyte pepsin-like enzyme was added to said human peripheral monocytes and they were cultured at 37° C. After 20 hours, the medium was changed to the same medium containing $2\times10^8$ sheep red blood cells, and the culture was effected for another 2 hours. The cells were then fixed with methanol followed by giemsa staining for calculating the rate of phagocytosis similarly as in Experimental Example 1. The results are set forth in Table 2.

TABLE 2

| Specimen | Concentration (μg/ml) | Rate of Phagocytosis |
|---|---|---|
| Eagle MEM only | — | 7.5 ± 0.6 |
| Human Pepsin | 0.6 | 8.5 ± 0.6 |
| | 6 | 9.6 ± 0.5* |
| Human Leukocyte Pepsin-like Enzyme | 6 | 9.5 ± 0.4* |

*P <0.05 (Student's t-test)

Human pepsin and human leukocyte pepsin-like enzyme promoted the phagocytosis of the sheep red blood cells by human monocytes. These results clearly indicate that human pepsin and human leukocyte pepsin-like enzyme potentiate the phagocytosis of phagocytes.

EXPERIMENTAL EXAMPLE 3

Influence on Human Monocytes' Activity to Transfer Immune Information to Lymphocytes Eagle MEM supplemented with 10% fetal bovine serum and containing human pepsin or a human leukocyte pepsin-like enzyme was added to $10^6$ cells/ml of human peripheral monocytes, and culture was effected for 20 hours. After the culture, the medium was changed to Eagle MEM supplemented with 10% fetal bovine serum and containing human pepsin or a human leukocyte pepsin-like enzyme and $2\times10^7$ cells/ml of sheep erythrocytes, and culture was effected at 37° C. for 30 minutes. After culturing, the medium was further changed to RPMI 1640 medium supplemented with 10% human serum and containing $3\times10^7$ cells/ml of human peripheral lymphocytes, and culture was effected for 7 days. After culturing, the lymphocytes were collected and the number of plaques was counted according to the method of Dosch et al., J. Immunol., 118, 302 (1972). The results are set forth in Table 3.

TABLE 3

| Specimen | Concentration (μg/ml) | Number of Plaques (/$10^6$ cells) |
|---|---|---|
| Eagle MEM only | — | 86 ± 11 |
| Human Pepsin | 0.6 | 97 ± 9 |
| | 6 | 138 ± 11* |
| Human Leukocyte Pepsin-like Enzyme | 6 | 131 ± 12* |

*P <0.05 (Student's t-test)

The human pepsin and the human leukocyte pepsin-like enzyme increased the production of the antibody against the sheep erythrocytes, i.e. a foreign matter to the lymphocytes. From these results, it has been made clear that human pepsin and the human leukocyte pepsin-like enzyme potentiate the phagocytes' activity to transfer immune information to lymphocytes.

EXPERIMENTAL EXAMPLE 4

Influence on Mouse Macrophages' Phagocytosis 5 ml of Eagle MEM supplemented with 10% fetal bovine serum and containing human pepsin, a human leukocyte pepsin-like enzyme or mouse pepsin was added to $10^6$ cells of mouse intraperitoneal macrophages, and they were cultured at 37° C. for 20 hours. After culture, the medium was changed to Eagle MEM supplemented with 10% fetal bovine serum and containing human pepsin, a human leukocyte pepsin-like enzyme or mouse pepsin and $2\times10^8$ cells of sheep erythrocytes or human erythrocytes, and culture was further effected for 2 hours. After culture, the macrophages were observed, and the rate of phagocytosis was calculated similarly as in Experimental Example 1. The results are set forth in Table 4.

TABLE 4

| Specimen | Concentration (μg/ml) | Rate of Phagocytosis (%) Sheep | Human |
|---|---|---|---|
| Eagle MEM only | — | 26.3 ± 2.1 | 53.1 ± 2.7 |
| Human Pepsin | 0.6 | 31.3 ± 2.2 | 45.8 ± 3.0 |
| | 6 | 35.0 ± 1.9* | 42.1 ± 2.4* |
| Human Leukocyte Pepsin-Like Enzyme | 6 | 34.7 ± 2.5* | 41.8 ± 2.7* |
| Mouse Pepsin | 6 | 35.1 ± 2.6* | 63.5 ± 2.3* |

*P <0.05 (Student's t-test)

The human pepsin and the human leukocyte pepsin-like enzyme increased the phagocytosis of the sheep erythrocytes by the mouse macrophages as the mouse pepsin did. However, in the mouse macrophages' phagocytosis of the human erythrocytes, both the human pepsin and the human leukocyte pepsin-like enzyme inhibited the phagocytosis while the mouse pepsin increased it. From these results, it has been clear that human pepsin and a human leukocyte pepsin-like enzyme have an effect to control phagocytic functions so as to increase the phagocytosis of heterogenic erythrocytes (sheep) but, on the contrary, inhibit the phagocytosis of allogenic erythrocytes (human).

EXPERIMENTAL EXAMPLE 5

Influence on Neutrophiles' Bactericidal Activity $2.6\times10^5$ cells of human peripheral leukocytes, $3\times10^8$ pieces of polystyrene latex particles, 50 μl of Nitroblue tetrazolium reagent and 150 μl of Crebs-Henseleit buffer containing human pepsin, a human leukocyte pepsin-like enzyme or an equal weight mixture of human pepsin and a human leukocyte pepsin-like enzyme were incubated at 37° C. for 15 minutes, and the absorbance of the mixed solution was measured at a wavelength of 710 nm according to a method of Okamura et al., Chem. Pharm. Bull., 24, 2175 (1976). The results are set forth in Table 5.

TABLE 5

| Specimen | Concentration (μg/ml) | Absorbance |
|---|---|---|
| Krebs-Henseleit Buffer Solution only | — | 0.132 ± 0.012 |
| Human Pepsin | 6 | 0.181 ± 0.020 |
| Human Leukocyte Pepsin-Like Enzyme | 6 | 0.175 ± 0.018 |
| Equal Mixture of Human Pepsin and Human Leukocyte Pepsin-like Enzyme | 6 | 0.180 ± 0.015 |

The human pepsin, the human leukocyte pepsin-like enzyme and the mixture thereof potentiated the bactericidal activity of the neutrophiles. From these results, it has been made clear that the effect to control phagocytic functions is observed not only in the case when the human pepsin or the human leukocyte pepsin-like enzyme is used alone but also in the case when they are used in combination.

EXPERIMENTAL EXAMPLE 6

Effect on Infectious Diseases Caused by Pseudomonas aeruginosa

Groups of 10 ICR strain mice, each weighing about 18 g, were intraperitoneally injected with $10^8$ cells of P. aeruginosa, IFO 3445 suspended in 0.2 ml of physiological saline. After one hour, physiological saline containing human serum albumin, human pepsin, a human leukocyte pepsin-like enzyme or an equal weight mixture of human pepsin and a human leukocyte pepsin-like enzyme was intravenously injected every day for 7 days, and the animals were observed for death or survival. The results are set forth in Table 6.

TABLE 6

| Specimen | Dosage (mg/kg) | Survival Rate (%) |
|---|---|---|
| Human Serum Albumin | 6 | 0 |
| Human Pepsin | 0.6 | 20 |
| | 6 | 40 |
| Human Leukocyte Pepsin-like Enzyme | 6 | 40 |
| Equal Mixture of Human Pepsin and Human Leukocyte Pepsin-like Enzyme | 6 | 40 |

The human pepsin, the human leukocyte pepsin-like enzyme and the mixture thereof exhibited a therapeutic effect with respect to infectious diseases.

EXPERIMENTAL EXAMPLE 7

Curing Action for Pulmonary Local Infection of E. coli

Groups of 10 ICR strain mice, each weighing about 15 g, were given intranasal administration of $10^9$ cells of E. coli (strain A4) suspended in 0.05 ml of physiological saline. One hour after the infection, a solution of a given amount of human serum albumin, human pepsin, human leukocyte pepsin-like enzyme or a mixture of human pepsin and human leukocyte pepsin-like enzyme in equal amounts dissolved in 0.1 ml of physiological saline was injected intravenously, the injection being continued daily for seven days. The survival of the animals was observed and the results are set forth in Table 7.

TABLE 7

| Specimen | Dosage (mg/kg) | Survival Rate (%) |
|---|---|---|
| Human Serum Albumin | 6 | 30 |
| Human Pepsin | 0.6 | 70 |
| | 6 | 90* |
| Human Leukocyte Pepsin-like Enzyme | 6 | 90* |
| Equal Mixture of Human Pepsin and Human Leukocyte Pepsin-like Enzyme | 6 | 90* |

*$P < 0.05$ ($\chi^2$-test)

Human pepsin, human leukocyte pepsin-like enzyme and the mixture thereof exhibited curing action for pulmonary local infection.

EXPERIMENTAL EXAMPLE 8

Curing Action for E. coli Infection on Immunosuppressed Mice

Groups of 10 ICR strain mice, each weighing about 20 g, were given intraperitoneally 200 mg/kg of cyclophosphamide dissolved in physiological saline at a concentration of 20 mg/ml. After four days, $3\times10^7$ cells of E. coli (strain A4) suspended in 0.2 ml of physiological saline were administered intraperitoneally. One hour after the infection, a solution of a given amount of human serum albumin, human pepsin, human leukocyte pepsin-like enzyme or a mixture of human pepsin and human leukocyte pepsin-like enzyme in equal amounts dissolved in 0.1 ml of physiological saline was administered intravenously, the administration being continued daily for seven days. The survival of the animals was observed and the results are set forth in Table 8.

TABLE 8

| Specimen | Dosage (mg/kg) | Survival rate (%) |
|---|---|---|
| Human Serum Albumin | 6 | 0 |
| Human Pepsin | 0.6 | 20 |
| | 6 | 40 |
| Human Leukocyte Pepsin-like Enzyme | 6 | 40* |
| Equal Mixture of Human Pepsin and Human Leukocyte Pepsin-like Enzyme | 6 | 40* |

*$P < 0.05$ ($\chi^2$-test)

Human pepsin, human leukocyte pepsin-like enzyme and the mixture thereof exhibited a curing action for E. coli infection on immunosuppressed mice.

EXPERIMENTAL EXAMPLE 9

Curing Action for Candida Infection

Groups of 10 ICR strain mice, each weighing about 15 g, were given intraperitoneal administration of $6\times10^8$ cells of C. albicans suspended in 0.2 ml of physiological saline. One hour after the infection, a solution of a given amount of human serum albumin, human pepsin, human leukocyte pepsin-like enzyme or a mixture of human pepsin and human leukocyte pepsin-like enzyme in equal amounts dissolved in 0.1 ml of physiological saline was administered intravenously, the administration being continued daily for seven days. The survival of the animals was observed and the results are set forth in Table 9.

TABLE 9

| Specimen | Dosage (mg/kg) | Survival rate (%) |
|---|---|---|
| Human Serum Albumin | 6 | 40 |
| Human Pepsin | 0.6 | 60 |
| | 6 | 80 |
| Human Leukocyte Pepsin-like Enzyme | 6 | 100* |
| Equal Mixture of Human Pepsin and Human Leukocyte Pepsin-like Enzyme | 6 | 90 |

*$P < 0.05$ ($\chi^2$-test)

Human pepsin, human leukocyte pepsin-like enzyme and the mixture thereof exhibited a curing action for Candida infection.

The infectious diseases studied in the foregoing Experimental Examples are considered representative of infectious diseases resulting from foreign matter invading or being generated in the body, e.g., microorganisms such as virus, bacteria, eumycetes, etc.

EXPERIMENTAL EXAMPLE 10

Influence on Cholesterol Deposition onto the Artery

Groups of 10 Wistar strain male rats, each weighing about 180 g, were fed with a 10% cholesterol added animal food. At the same time with the start of feeding, 0.1 ml of physiological saline containing human serum albumin, human pepsin, a human leukocyte pepsin-like enzyme or an equal weight mixture of human pepsin and a human leukocyte pepsin-like enzyme was intravenously injected every day. After three months, the animals were killed, and the arteries were collected. One hundred mg of the arteries were freeze-dried, extracted with 20 volumes of methanol-chloroform (1:3), and 5 ml of the extract was dried in nitrogen gas. The cholesterol in the residue was measured using a Wako cholesterol kit (trade mark). The results are set forth in Table 10.

TABLE 10

| Specimen | Dosage (mg/kg) | Cholesterol (mg/100 g - Artery) |
|---|---|---|
| Human Serum Albumin | 6 | 112 ± 18 |
| Human Pepsin | 0.6 | 91 ± 20 |
| | 6 | 50 ± 11* |
| Human Leukocyte Pepsin-like Enzyme | 6 | 51 ± 9* |
| Equal Mixture of Human Pepsin and Human Leukocyte Pepsin-like Enzyme | 6 | 48 ± 14* |

*$P < 0.05$ (Student's t-test)

The human pepsin, the human leukocyte pepsin-like enzyme and the mixture thereof inhibited the cholesterol deposition onto the arteries and exhibited a therapeutic effect on arteriosclerosis.

EXPERIMENTAL EXAMPLE 11

Influence on Inflammation caused by Urate Crystals 10 mg of sodium urate crystals were injected into the left foreleg joint of each male dog, 3 animals in each group, weighing about 10 kg immediately followed by intravenous injection of 10 ml of physiological saline containing human serum albumin, human pepsin, a human leukocyte pepsin-like enzyme or an equal weight mixture of human pepsin and a human leukocyte pepsin-like enzyme. For the following 24 hours, the walking conditions of the dogs were observed. The results are set forth in Table 11.

TABLE 11

| Specimen | Dosage (mg/kg) | Observation |
|---|---|---|
| Human Serum Albumin | 6 | Walked using 3 legs for 1-6 hours after injection |
| Human Pepsin | 6 | No abnormality |
| Human leukocyte Pepsin-like Enzyme | 6 | No abnormality |
| Equal Mixture of Human Pepsin and Human Leukocyte Pepsin-like Enzyme | 6 | No abnormality |

The human pepsin, the human leukocyte pepsin-like enzyme and the mixture thereof inhibited the walking abnormality due to the urate and exhibited a therapeutic effect on gout.

EXPERIMENTAL EXAMPLE 12

Acute Toxicity Test

Groups of 10 ddY strain male mice, each weighing 20–25 g, were administered either intravenously or intraperitoneally with 2 g/kg of human pepsin, a human leukocyte pepsin-like enzyme or an equal mixture thereof dissolved in physiological saline, and the severity of the conditions were observed for a week. No abnormality was observed.

As clear from the experimental examples described above, human pepsin and a human leukocyte pepsin-like enzyme which are main ingredients in the pharmaceutical compositions of this invention exhibit an effect to control phagocytic functions, and at the same time have an effect to treat various diseases related to phagocytic functions such as tumors, allergies, infectious diseases, autoimmune diseases, immunodeficiency, arteriosclerosis, gout, etc. The dosages thereof are sufficiently safe amounts as guaranteed from the result of the acute toxicity test. Further, since they are human-derived proteins, it is also believed that there is only little risk of bringing about severe side effects owing to antigenicity such as anaphylaxis shock, etc. Thus they are believed to be extremely clinically useful agents for various tumors. The therapeutic agents of this invention are generally administered as injections, intravenously, intraarterially, subcutaneously, intramuscularly, topically, etc., and also they may be employed as oral preparations, inhalants, rectal suppositories, etc. The therapeutic dosage of the human pepsin or the human leukocyte pepsin-like enzyme for a human adult is 1–1000 mg, preferably 5–500 mg/day, which may be appropriately varied depending on the severity of the disease or the use method. Furthermore, the human pepsin and the human leukocyte pepsin-like enzyme may be employed in combination at any ratio.

Human pepsin and a human leukocyte pepsin-like enzyme may be formulated into pharmaceutical preparations in a conventional manner together with optional and conventional pharmaceutical carriers or excipients.

Examples of solid carriers and excipients usable advantageously herein include common excipients such as lactose, mannitol, corn starch and potato starch; binders such as crystalline cellulose, cellulose derivatives, arabic gum, corn starch and gelatin; disintegrators such as corn starch, potato starch and calcium carbohydroxymethylcellulose; and lubricants such as talc and magnesium stearate. Examples of liquid carriers usable advantageously herein include distilled water for injection, physiological saline solution, vegetable oils for injection and glycols such as propylene glycol and polyethylene glycol.

Preferred examples of the injections include freeze-dried preparations which may be dissolved before use and injectable liquid preparations; those of the oral preparations include capsules, tablets, granules, powders and oral liquid preparations; those of inhalants include freeze-dried powders and those of the preparations for rectal administration include rectal suppositories.

Examples of this invention are illustrated hereinbelow.

EXAMPLE 1

100 mg of human pepsin was dissolved in 10 ml of physiological saline and aseptically filtered using a membrane filter. The filtrate was placed in sterilized glass containers, 1.0 ml each, then freeze-dried and sealed to prepare freeze-dried powder preparations.

EXAMPLE 2

100 g of freeze-dried human pepsin, 97 g of lactose and 3 g of magnesium stearate were weighed respectively and mixed uniformly. This mixture was placed in No. 2 gelatin capsules, 200 mg each, and provided with enteric coating to give enteric capsules.

EXAMPLE 3

100 mg of a human leukocyte pepsin-like enzyme was dissolved in 10 ml of physiological saline and aseptically filtered using a membrane filter. The filtrate was placed in sterilized glass containers, 1.0 ml each, and then freeze-dried to prepare freeze-dried powder preparations.

EXAMPLE 4

Egg yolk lecithin, cholesterol and diacetyl phosphate were mixed at a molar ratio of 7:2:1, then 100 mg thereof was dissolved in 12.5 ml of chloroform, and a thin film was formed on a flask wall. This film and 25 ml of phosphate buffer containing 50 mg of human pepsin and 50 mg of a human leukocyte pepsin-like enzyme were mixed to prepare a dispersion. This was ultrasonically treated and centrifuged at 110,000×g, and the resulting precipitates were suspended in 3 ml of physiological saline and sterilized, thereby obtaining a preparation filled with a liposome containing an equal weight mixture of the human pepsin and the human leukocyte pepsin-like enzyme.

What is claimed is:

1. A pharmaceutical composition having an effect to control phagocytic function, which comprises a phagocytic function controlling effective amount of a human leukocyte pepsin-like enzyme having a molecular weight of 35,000–41,000, an isoelectric point of 2.5–3.5, a maximum absorption of 278 nm, giving a positive ninhydrin reaction and being readily soluble in water and insoluble in ether and chloroform, and a pharmaceutically acceptable carrier.

2. The pharmaceutical composition according to claim 1 which is a water soluble injection solution or a freeze dried injection solution.

3. The pharmaceutical composition according to claim 1 which is in the form of capsules, tablets, granules, powder or an oral liquid preparation.

4. The pharmaceutical composition according to claim 1 which is in the form of an inhalant or suppository.

5. The pharmaceutical composition according to claim 1 in which the composition is in the form of a dosage unit containing 1-1000 mg of said human leukocyte pepsin-like enzyme.

6. The pharmaceutial composition according to claim 5 in which the composition is in the form of a dosage unit containing 5-500 mg of said human leukocyte pepsin-like enzyme.

7. A method for treating infectious diseases, gout or arteriosclerosis, which comprises administering a therapeutically effective amount of human pepsin and/or a human leukocyte pepsin-like enzyme to a patient suffering from an infectious disease, gout or arteriosclerosis.

8. The method according to claim 7 in which the human pepsin has a molecular weight of 32,000-38,000, an isoelectric point of 1-3, a maximum absorption of 274 nm, gives a positive ninhydrin reaction and is readily soluble in water and insoluble in ether and chloroform.

9. The method according to claim 7 in which the human leukocyte pepsin-like enzyme has a molecular weight of 35,000-41,000, an isoelectric point of 2.5-3.5, a maximum absorption of 278 nm, gives a positive ninhydrin reaction and is readily soluble in water and insoluble in ether and chloroform.

10. The method according to claim 7 in which the human pepsin is derived from a human stomach or human urine.

11. The method according to claim 7, which comprises administering the human pepsin and/or the human leukocyte pepsin-like enzyme by injection.

12. The method according to claim 7, which comprises orally administering the human pepsin and/or the human leukocyte pepsin-like enzyme.

13. The method according to claim 7, which comprises administering the human pepsin and/or human leukocyte pepsin-like enzyme transmucosally or by inhalation.

14. The method according to claim 7, which comprises administering 1-1000 mg/day of the human pepsin and/or the human leukocyte pepsin-like enzyme.

15. The method according to claim 14, which comprises administering 5-5000 mg/day of the human pepsin and/or the human leukocyte pepsin-like enzyme.

* * * * *